United States Patent [19]
Lundstrom et al.

[11] Patent Number: 6,093,269
[45] Date of Patent: *Jul. 25, 2000

[54] PYROTECHNIC GAS GENERANT COMPOSITION INCLUDING HIGH OXYGEN BALANCE FUEL

[75] Inventors: Norman H. Lundstrom, Manassas; Aaron J. Greso, Culpeper; Robert S. Scheffee, Lorton, all of Va.

[73] Assignee: Atlantic Research Corporation, Gainesville, Va.

[*] Notice: This patent is subject to a terminal disclaimer.

[21] Appl. No.: 08/993,882

[22] Filed: Dec. 18, 1997

[51] Int. Cl.$^7$ ................................................ C06B 29/00
[52] U.S. Cl. ............................. 149/36; 149/61; 149/76; 149/19.1
[58] Field of Search ................... 149/36, 76, 61, 149/19.1

[56] References Cited

U.S. PATENT DOCUMENTS

| | | | |
|---|---|---|---|
| 3,405,144 | 10/1968 | Brownlee | 260/349 |
| 3,723,205 | 3/1973 | Scheffee | 149/19.91 |
| 3,813,439 | 5/1974 | Picard et al. | 149/36 |
| 3,819,380 | 6/1974 | Baldassarri et al. | 96/76 R |
| 4,369,079 | 1/1983 | Shaw | 149/2 |
| 4,370,181 | 1/1983 | Lundstrom et al. | 149/2 |
| 4,909,549 | 3/1990 | Poole et al. | 149/2 |
| 4,948,439 | 8/1990 | Poole et al. | 149/46 |
| 5,035,757 | 7/1991 | Poole | 149/46 |
| 5,084,118 | 1/1992 | Poole | 149/22 |
| 5,139,588 | 8/1992 | Poole | 149/61 |
| 5,386,775 | 2/1995 | Poole et al. | 149/36 |
| 5,399,555 | 3/1995 | Vandevelde et al. | 514/150 |
| 5,557,062 | 9/1996 | MacLaren et al. | 149/61 |
| 5,656,793 | 8/1997 | Ochi et al. | 149/36 |
| 5,811,725 | 9/1998 | Klager | 149/19.4 |
| 5,861,571 | 1/1999 | Scheffee et al. | . |
| 5,883,330 | 3/1999 | Yoshida | 149/36 |

OTHER PUBLICATIONS

Johannes Thiele in "Justus Liebig's Annalen Der Chemie" 270. (Partial translation).

*Primary Examiner*—Edward A. Miller
*Attorney, Agent, or Firm*—Nixon & Vanderhye P.C.

[57] ABSTRACT

A pyrotechnic gas generant composition including a high oxygen balance compound or fuel which is the resulting reaction product of aminoguanidine nitrate and nitric acid. Specifically, the resulting reaction product is a yellow precipitate that can be used alone, with or without oxidizers or other additives, for very rapid self-deflagration or in combination with oxidizers and additives. In each instance, the gas generant composition provides both high gas output and low production of solid combustion products. Further, the precipitant is relatively non-hygroscopic and has a high burn rate. Specifically, the gas generating composition is useful as a gas generator for an air bag of an occupant restraint system for an automobile, gun propellants, inflation and expulsion devices, flotation devices, pyrotechnics, fire suppression devices and smokeless, reduced smoke and smokey rocket propellants.

24 Claims, 3 Drawing Sheets

PYROTECHNIC GAS GENERANT COMPOSITION INCLUDING HIGH OXYGEN BALANCE FUEL

BACKGROUND OF THE INVENTION

1. Field of the Invention

The present invention relates to ingredients for use in pyrotechnic gas generant compositions, and more specifically to fuels containing a high oxygen balance. The gas generant compositions are useful as gas generant propellants for air bag occupant restraint systems for automobiles, gun propellants, inflation and expulsion devices, flotation devices, ignition materials, pyrotechnics, fire suppression devices and smokeless and smoke producing rocket propellants.

2. Background Art

There is high demand for pyrotechnic gas generant compositions which on combustion yield acceptable burning rates and provide, at relatively low flame temperatures, a high volume of substantially non-toxic gas and a low volume of solid particulate matter that can produce smoke. It is also important that resulting solid by-products from the combustion of gas generant compositions be minimal, and the gaseous combustion products be substantially non-toxic, and non-corrosive. Various compositions of gas generants have been utilized in the past in an attempt to reach the above desirable characteristics.

U.S. Pat. No. 3,405,144 discloses a 1-azido-N,N,N'-trifluoroformamidine that is useful in a propellant composition which exhibits a high specific impulse. Specifically, the said material is disclosed to be useful in rocket fuel compositions. Gas generant compositions have also been developed to include the addition of modifiers to lower flame temperatures and increase gas production. Further ingredients may be added such as binders, ignition aids, slag formers, scavengers, and catalysts to improve various features of the underlying propellant. The modifiers and additional ingredients often times, however, improve one aspect of the propellant composition while also contributing to the production of undesirable by-products and may increase the corrosiveness thereof. This is particularly disadvantageous in an automobile air bag environment.

One major gas generating composition having desirable characteristics contains strontium nitrate and 5-aminotetrazole (SrN/5ATZ) as major constituents. This formulation is relatively non-toxic when compared with sodium azide systems, has good ballistic properties and retains the majority of solid combustion products as a slag or clinker either in the combustion or filtration areas of, for instance, an air bag system for an automobile. These formulations also exhibit acceptable flame temperatures of 2250° K. to 2750° K. depending upon the stoichiometry of the formulation and the oxygen to fuel ratio. Moreover, the strontium nitrate and 5-aminotetrazole formulations are relatively non-hygroscopic and the ingredients do not exhibit crystalline phase changes over the operating temperature range of the air bag system.

Such a formulation, however, suffers with regard to gas output, specifically, in the volume limited systems of a driver's side air bag. This is because a high concentration of strontium nitrate is required to maintain a neutral oxygen to fuel (O/F) balance. Because inflator designs are becoming smaller and smaller and, thus, more volume limited, propellants are required to provide greater gas output and still retain the desirable attributes of the strontium nitrate/5-aminotetrazole systems.

Approaches have been taken to obtain the attractive features of the above-noted propellants, while overcoming the low gas output thereof. This has resulted in the development of propellants based on mixtures of potassium perchlorate and oxygenated fuels such as guanidine nitrate and aminoguanidine nitrate. These propellants are also relatively non-hygroscopic, provide excellent gas output, high burning rates and only about two thirds of the solid combustion products of the above-noted strontium nitrate and 5-aminotetrazole based propellants. Unfortunately, the solid combustion products do not form clinkers or slags which deposit in the combustion or filtration area, but instead form very fine particulates in the gas stream which results in a smokey and dirty exhaust.

Smoke or dirty exhaust combustion products are not commercially desirable, particularly, in automobile air bag systems since the production of such product may cause undue anxiety on the part of drivers and passengers involved in an automobile accident in which air bags are deployed. As a result, there is a need for a propellant material or gas generant that exhibits high gas output upon combustion, but does not produce unwanted by-products upon combustion.

SUMMARY OF THE INVENTION

The object of the present invention is to improve upon and to overcome the deficiencies of the prior art and to provide a substantially non-hygroscopic, substantially non-toxic gas producing pyrotechnic gas generant composition that upon combustion produces a high gas output and a high burn rate with limited non-gaseous combustion products.

Another object of the present invention is to provide a pyrotechnic gas generant composition including a high oxygen balance fuel that produces the desirable high gas output at a low combustion temperature and reduced non-gaseous combustion products.

Still another object of the present invention is to provide a pyrotechnic gas generant composition including a high oxygen balance fuel with the capability of self-deflagration similar to a solid monopropellant.

Yet another object of the present invention is to provide a pyrotechnic gas generant composition including a high oxygen balance fuel which will auto-ignite in an inflator at acceptable but low enough temperatures to ensure that the inflator only rupture but does not fragment in a bonfire test.

Still another object of the present invention is to provide a gas generating composition capable of producing a substantially high gas output upon combustion for use as an automobile air bag propellant. However, the composition of the present invention may also be employed to inflate such items as an inflatable raft or passenger escape chute of an airplane, as well as for gun propellants, pyrotechnics, ignition mixtures, fire suppression devices and rocket propellants. From a practical standpoint, the composition of the present invention also may include additives heretofore used with other gas generant compositions, such as oxidizers, gas conversion catalysts, ballistic modifiers, slag formers, ignition aids, energetic plasticizers and binders, non-energetic binders, and compounding aids.

The foregoing objects are generally achieved by a pyrotechnic gas generant composition including a high oxygen compound or fuel which is the resulting reaction product of aminoguanidine nitrate and nitric acid. Specifically, the reaction product is a yellow precipitate that can be ignited and used alone, with no oxidizers or other additives, for very rapid and substantially smokeless self-deflagration or combusted in combination with oxidizers and/or other additives.

In each instance, the gas generant composition provides both high gas output and low production of solid decomposition products upon combustion. Further, the precipitate is relatively non-hygroscopic and has a high burn rate. As a result, cartridges used to contain the gas generating composition are not required to withstand the extremely high pressures associated with prior art gas generating compositions, such as ammonium nitrate based compositions, that exhibit the similar low solid combustion product production as the gas generating composition of the present invention, but have low burn rates and are generally hygroscopic.

Based upon the general physical characteristics of the above-noted reaction product of the present invention, the product is believed to be 1,1'-azodiformamidine dinitrate. However, the pyrotechnic gas generant composition of the present invention is directed separately to both the use of the yellow reaction product of aminoguanidine nitrate and nitric acid and to 1,1'-azodiformamidine dinitrate.

The gas generant composition of the present invention is generally prepared by the methods heretofore employed for prior art compositions and generally, but not exclusively, involve the dry or wet blending and compaction of the comminuted ingredients selected for combination. In view of the advantageous characteristics of the gas generant composition of the present invention, namely, high gas output, low solid combustion products production and high burn rate, the generant has applications in automobile air bag systems, inflatable rafts or passenger escape chutes, gun propellants, pyrotechnics, ignition mixtures, fire suppression devices and rocket propellants.

For purposes of the present invention, the terms propellant(s) and gas generant(s) are used interchangeably. Also, for the purposes of this invention, the reactions shown are with anhydrous components. The use of non-anhydrous components, however, is also contemplated.

DETAILED DESCRIPTION OF THE PREFERRED EMBODIMENTS

The invention provides for a pyrotechnic gas generant, which when combusted provides high gas output and minimal solid combustion products and which is useful for various purposes. It has been found that the reaction of the high oxygen balance fuel of the present invention with an oxidizer produces a high gas output volume with very little solid combustion products. In addition, the fuel also exhibits a high burn rate and is a self-deflagrating monopropellant. As a result, the gas generant composition of the present invention can be a single ingredient auto-ignition pill (AIP); a solid monopropellant; a high oxygen balance fuel in all pyro systems; a burning rate enhancing additive; and an ingredient in conventional and oxygenated hybrid inflation systems. As one can see, the gas generant of the present invention is particularly useful as an automobile air bag propellant, but also has applications as a gun propellant, flotation device gas generant, propellant, pyrotechnic, gas generator, ignition mixture, fire suppression device and rocket propellant.

Additional objects and advantages of the present invention will become readily apparent to those skilled in the art from the following detailed description wherein the preferred embodiments of the invention are shown and described simply by way of illustration of the best mode contemplated for carrying out the invention. As will be realized, the invention is capable of other and different embodiments and its several details are capable of modifications of various obvious respects, all without departing from the invention. Accordingly, the figures and description are to be regarded as illustrative in nature and not as restrictive.

More specifically, the gas generant composition of the present invention includes a high oxygen balance formamidine-type fuel prepared from the reaction of nitric acid and aminoguanidine nitrate. The inventors believe the fuel to be azodiformamidine dinitrate (also called azodicarbamidine dinitrate, azobicarbamidine dinitrate, and azobisformamidine dinitrate) shown structurally as follows:

This invention is not limited, however, to only azodiformamidine dinitrate, but instead is also directed to the product from the reaction of nitric acid and aminoguanidine nitrate as provided in detail below.

With regard to azodiformamidine dinitrate, reference is made to J. Thiele, Ann 270, 39 (1892) which describes this compound as azodicarbonamidinnitrat. This previous synthesis was done, however, in conjunction with an investigation of materials for potential woolen dyes/pigments, which is entirely different from the present invention.

Moreover, the prior synthesis involved the addition of a solution of a metallic oxidizing compound (potassium permanganate) to form a yellow reaction product and did not add heat from an external source during the process. The method of the present invention, as provided below, is preferred because by adding heat, the reaction occurs rapidly without requiring the addition of a metal oxidizing compound. By avoiding the use of a metal oxidizing compound during the preparation of the yellow reaction product, the high oxygen fuel gas generant of the present invention can be prepared free of foreign solid minute particles or without the potential for formation of metallic oxide particles. Thus, gas generants using the high oxygen balance fuel of the present invention can be prepared without metal-containing contaminants.

The reaction of the present invention will also occur without external heat or use of potassium permanganate at ambient temperature if nitric acid and aminoguanidine nitrate are allowed to digest over a longer period of time.

Hydrazodicarbonamidine, diazoguanidine, formamidine, bisformamidine, and azobisformamidine derivative fuels such as diazoguanidine nitrate, azobisnitroformamidine, and 1,1'-azodiformamidine dipicrate are also useful gas generator ingredients. In addition, other derivatives and fuels containing a formamidine, diazoguanidine, or hydrazodicarbonamidine group with an oxidizing group, e.g. $(NO_2)$, $(NO_3)$, $(ClO_4)$, $(ClO_3)$, or mixtures of oxidizing groups, or mixtures of different hydrazodicarbonamidine, diazoguanidine, formamidine, bisformamidine, and azobisformamidine compounds, with proper precautionary measures, are also useful in propellant compositions.

Prior art propellants, such as those containing ammonium nitrate, produce very little solid combustion products, but have a number of other properties that make them less desirable. Ammonium nitrate, for instance, is hygroscopic. Moreover, in gas generant/propellant compositions, its use results in a low burn rate and a high pressure exponent at operating pressures of 1000–2000 psi. Consequently, a propellant composition including ammonium nitrate as the principal oxidizer must be burned at very high pressures, e.g. 4000–6000 psi, and sealed to prevent moisture from contacting the composition. In addition, ammonium nitrate typically requires the use of phase stabilizers, such as potassium compounds, which generate solid combustion products.

The high oxygen balance fuel of the present invention overcomes a number of the above-noted, less than desirable characteristics. Specifically, a gas generantipropellant composition including the high oxygen balance fuel of the present invention exhibits a high gas output with no or little resulting solid combustion product or ash, while also being relatively non-hygroscopic, having a high burn rate and providing a more desirable pressure exponent. As a result, the composition of the present invention does not have to be held in such a high pressure and moisture sealed container, since the operating pressures required for achieving burning rates are much lower than for the above-noted ammonium nitrate gas generant propellant compositions.

The gas generant composition of the present invention can function alone as a self-deflagrating monopropellant, as noted above, or include an oxidizer. Other materials may be added to the composition for processing, aiding ignition, enhancing ballistics, improving thermal aging and stability, improving hazardous properties, reducing particulates, binding, and scavenging undesirable gaseous combustion products.

A single oxidizer or multiple oxidizers may be combined with the high oxygen balance fuel of the present invention to supply additional oxygen for achieving the desired oxygen to fuel balance (O/F) during combustion. Since the high oxygen balance fuel of the present invention includes a larger amount of oxygen than prior gas generating compositions, a smaller amount of oxidizer for providing a desirable oxygen to fuel (O/F) balance is necessary. Suitable metallic and non-metallic oxidizers are known in the art and generally comprise nitrites, nitrates, chlorites, chlorates, perchlorates, oxides, peroxides, persulfates, chromates and perchromates of non-metals, alkali metals, alkaline earth metals, transition metals and transition metal complexes and mixtures thereof. Preferred oxidizers include ammonium perchlorate, potassium perchlorate, strontium nitrate, potassium nitrate, sodium nitrate, barium nitrate, potassium chlorate, and mixtures thereof.

Preferred oxidizers are non-hygroscopic in order to preserve the advantageous characteristic of the high oxygen balance fuel of the present invention. The preferred oxidizers are generally employed in a concentration of about 0% to 98% by weight of the total gas generant composition and preferably in a concentration of 5 to 50% by weight of the total gas generant composition.

Scavengers may be desirable to control the production of corrosive combustion iu products. For example, if a non-metal oxidizer is used, such as ammonium perchlorate, hydrogen chloride (HCl) can be produced as a resulting reaction product, which is clearly undesirable. To prevent the production of HCl, a scavenger such as sodium nitrate can be used to form sodium chloride (NaCl) instead. Toxic gas scavengers may also be employed.

The combustion of the high oxygen balance fuel of the present invention may also be controlled by the addition of ballistic modifiers and include burning rate catalysts which influence the temperature sensitivity, pressure exponent and rate at which the propellant bums. Such ballistic modifiers were primarily developed for solid rocket propellants, but have also been found useful in gas generants for inflatable devices. Examples of ballistic modifiers useful with the composition of the present invention include oxides and halides of Group 4 to 12 of the Periodic Table of Elements (as developed by IUPAC and published by the CRC Press, 1989); sulfur and metal sulfides; transition metal salts containing copper, chromium, cobalt, nickel and mixtures thereof; and alkali metal and alkaline earth metal borohydrides. Guanidine borohydrides and triaminoguanidine borohydrides have also been used as ballistic modifiers. Organometallic ballistic modifiers include metallocenes, ferrocenes and metal acetyl acetonates. Other ballistic modifiers include salts of dicyanamide, nitroguanidine, guanidine chromate, guanidine dichromate, guanidine trichromate, and guanidine perchromate. The ballistic modifiers are generally employed in concentrations varying from about 0.1 to 25% by weight of the total gas generant composition. Because of the self-deflagrating, high burning rate characteristics of the high oxygen fuel of the present invention, low concentrations of said fuel, namely, 0.1–25% can be incorporated for use as a ballistic modifier in other gas generant compositions.

Filterable slag formation can be enhanced by the addition of a slag former. Such a slag former may not, however, be necessary in the present invention in view of the limited amount of solid combustion product produced. Suitable slag formers, if deemed necessary, include lime, borosilicates, vycor glasses, bentonite clay, silica, alumina, silicates, aluminates, transition metal oxides, alkaline earth compounds, lanthanide compounds, and mixtures thereof.

Another additive found to aid in the ease and temperature of ignition and resulting combustion of gas generant compositions is an ignition aid. Ignition aids include finely divided elemental sulfur, boron, boron-potassium nitrate ($BKNO_3$), carbon, magnesium, aluminum, and Group 4 transition metals, transition metal oxides, hydrides and sulfides, the hydrazine salt of 3-nitro-1,2,4-triazole-5-one and mixtures thereof. The ignition aids are normally employed in concentrations of 0.1 to 15% by weight of the total gas generant composition.

It may be desirable to add compounding agents to facilitate compounding and obtain homogeneous mixtures. Suitable binders and processing or compounding aids include molybdenum disulfide, graphite, boron nitride, alkali metal, alkaline earth and transition metal stearates, polyethylene glycols, polyacetals, polyvinyl acetates, polyvinyl alcohols, polycarbonates such as Q-PAC, fluoropolymers commercially available under the tradename TEFLON, and silicones. The compounding aids are typically employed in concentrations of about 0.1 to 15% by weight of the total gas generant composition.

In addition to the above-noted additives, the high balance fuel of the present invention may also be combined with other fuels and/or energetic nitro and/or nitrato plasticizers and/or energetic and non-energetic binders to provide a gas generant/propellant composition. Suitable fuels for such combination with the fuel of the present invention include but are not limited to the families of azido, hydrazine, guanidine, tetrazole, triazole, triazine, polyamine, nitramine (linear and cyclic), and derivatives of these families of fuels, as well as mixtures thereof. Suitable energetic plasticizers include but are not limited to butanetriol trinitrate (BTTN), nitroglycerine (NG), triethyleneglycol dinitrate (TEGDN), trimethylolethane trinitrate (TMETN) and mixtures thereof. An example of an energetic binder includes glycidyl azide polymer (GAP).

The manner and order in which the components of the gas generant composition of the present invention are combined and compounded are not critical so long as an intimate, uniform mixture with good structural integrity is obtained and the compounding is carried out under conditions which are not unduly hazardous, and, which do not cause decomposition of the components employed. For example, the materials may be wet blended in aqueous or nonaqueous liquids, or dry blended, with or without binders or processing aids, in a ball mill or "RED DEVIL" type paint shaker and then extruded, pelletized by compression molding, or formed into a castable or compression molded monolithic grain. The materials may also be ground separately or together with or without binders and/or other additives in a fluid energy mill, "SWECO" vibroenergy mill, or bantam micro-pulverizer and then blended or further blended in a v-blender prior to compaction.

The various components described hereinabove for use with the novel high oxygen balance fuel of the present invention have been used heretofore in other gas generant compositions. References involving gas generant compositions describing various additives include U.S. Pat. Nos. 5,035,757; 5,084,118; 5,139,588; 4,948,439; 4,909,549; and 4,370,181. As taught in this art and as will be apparent to those skilled in the art, it is possible to combine the functions of two or more additives into a single composition. Thus, alkaline earth metal salts of tetrazoles, bitetrazoles and triazoles not only function as gas generant components but can also be used as slag formers. It has also been found that strontium nitrate, for instance, acts not only as an oxidizer and a slag former, but also is effective as a ballistic modifier, ignition aid, densifier and processing aid.

The high oxygen balance fuel of the present invention can utilize conventional gas generator mechanisms of the prior art. These are referred to in U.S. Pat. No. 4,369,079, incorporated herein by reference. Generally, the methods of the prior art involve the use of a hermetically sealed metallic cartridge containing a gas generant composition. Hydrazodicarbonamidine, diazoguanidine, formamidine, bisformamidine, and azobisformamidine type fuels of the present invention can be used in such devices. Specifically, upon initiation of combustion by the firing of a squib, the sealing mechanism ruptures. This allows gas to flow out of the combustion chamber through several orifices. Of course, other gas generator mechanisms may equally be employed for use with the gas generant composition of the present invention.

Figure 1:
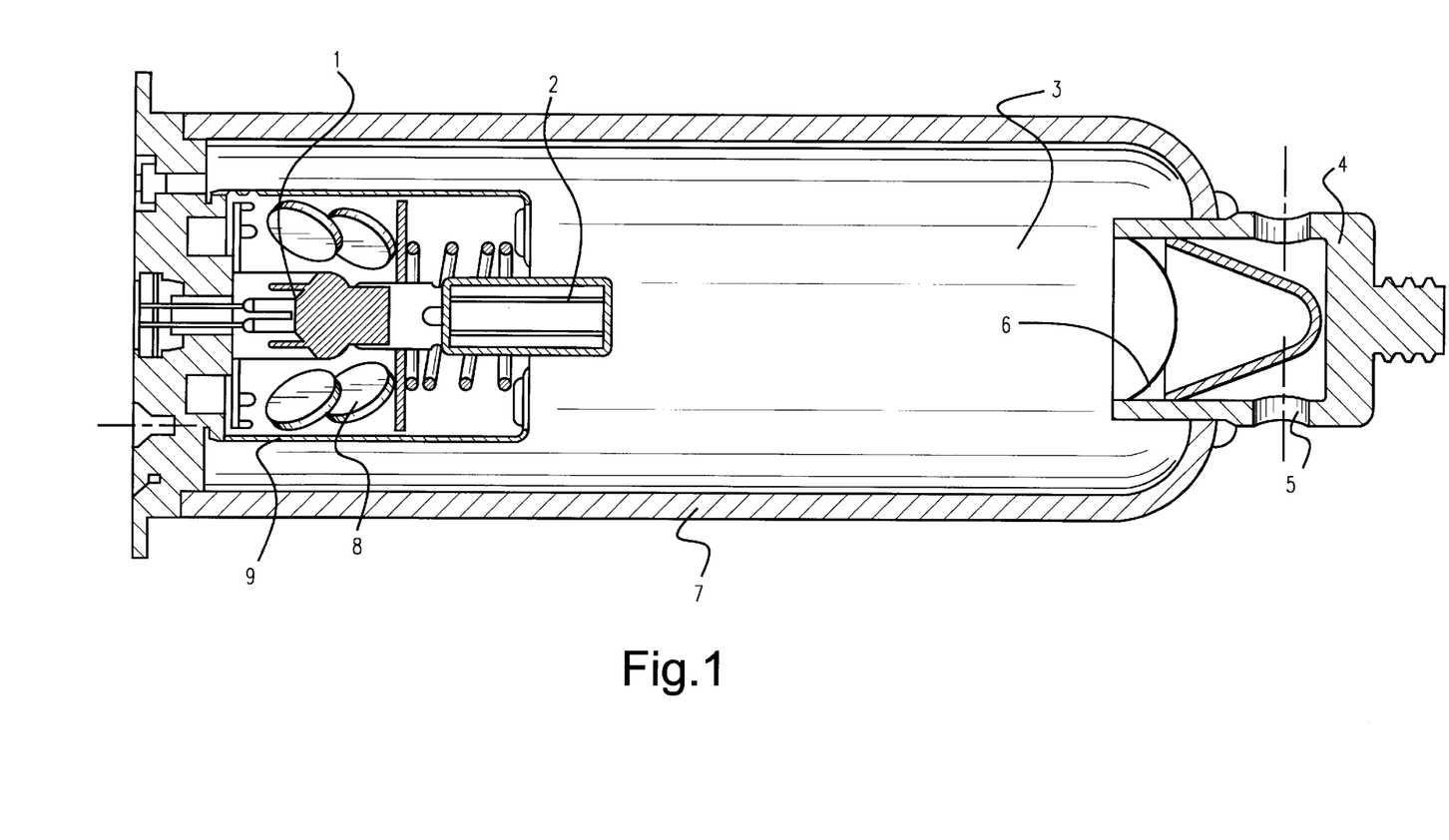
FIG. 1 is a conventional passenger-side inflator that may be used with the composition of the present invention.

With reference to an automobile air bag environment, FIG. 1 depicts a conventional passenger-side hybrid inflator for an automobile in which the high oxygen balance fuel of the present invention may be used. In practice, the initiator 1 ignites in response to a sensor (not shown) that senses rapid deceleration indicative of a collision. The initiator gives off hot gases that ignite the ignition charge 2 which causes the main generant charge 8 to combust, thereby heating and further pressurizing the inflation gas mixture 3. When the pressure in the inflation gas mixture increases to a certain point, the seal disk 6 ruptures, permitting the gas mixture to exit the manifold 4 through the outlet portions 5 and inflate an air bag. The generant container 9 holds the main generant charge 8. All the charges in the inflation gas mixture are enclosed in the pressure tank 7.

Figure 2:
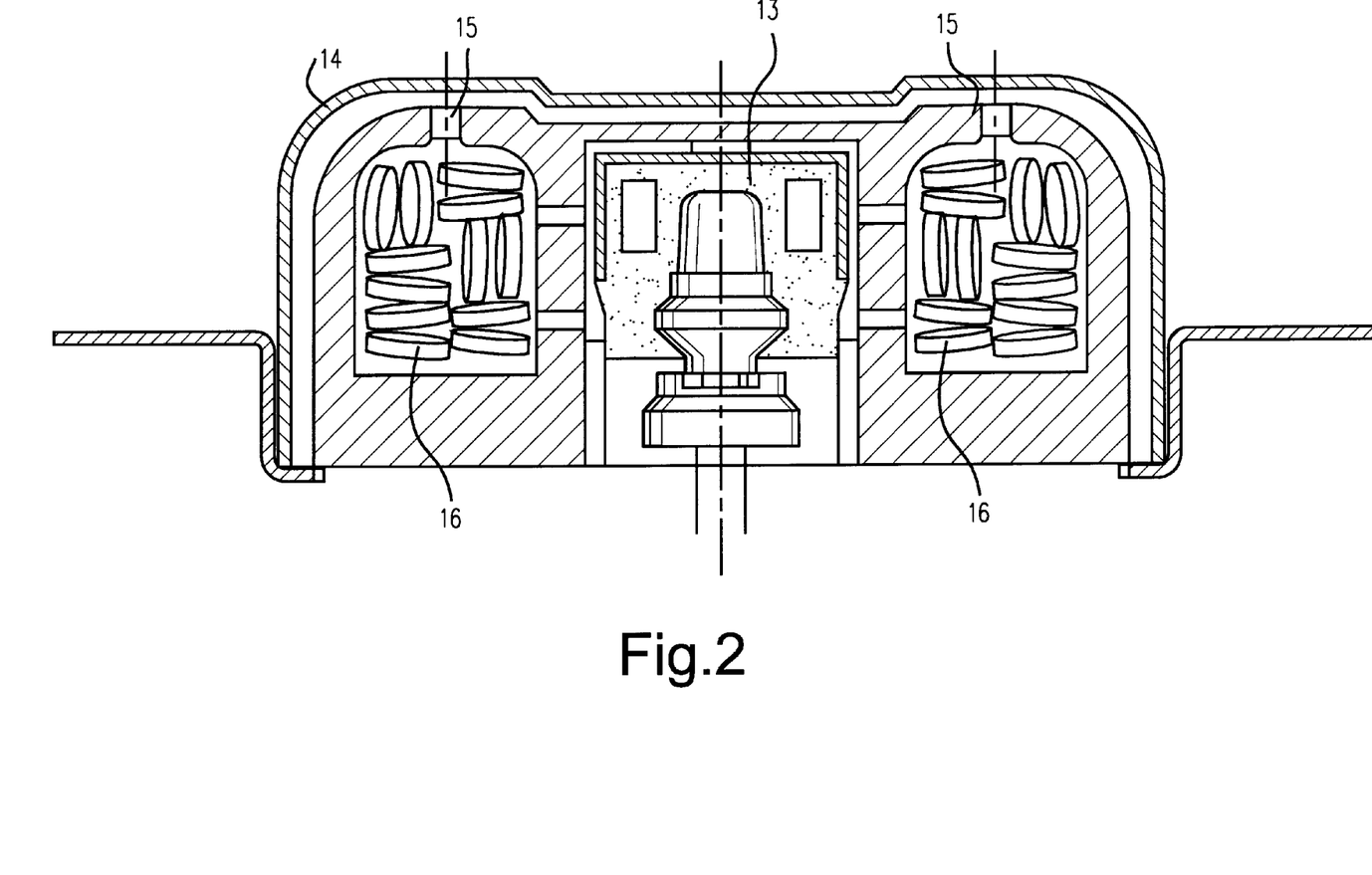
FIG. 2 is a conventional driver-side inflator that may be used with the composition of the present invention.

FIG. 2 illustrates an all pyrotechnic gas generator in which the instant invention may be employed. Since no part of the inflator is reserved for storage capacity, the device is smaller than its counterpart hybrid inflator. In this figure, there is an initiator 11 that will combust in response to a signal from a sensor (not shown), that generates a signal as a result of a change in conditions, e.g., an excessive increase in temperature or a sudden deceleration of a vehicle (indicative of a crash), in which the inflator is installed. The initiator 11 gives off hot gases that ignite the main generant charge 16, which combusts, generating an inflation gas mixture. The mixture exits the manifold 14 through the exit ports 15. To insure that the gas generating propellant 16 will be ignited well below its auto-ignition temperature ($T_{ig}$) and well below that temperature where the materials of construction of the hardware begin to weaken, an auto-ignition propellant (AIP) 13 having a suitably low $T_{ig}$ may be needed to ignite the ignition charge 12, which then ignites the propellant 16.

Because of the high burning rates exhibited by the high oxygen balance fuel of the present invention at moderate to low operating pressures, the invention may also be utilized in the physical form of a monolithic grain.

Use of the high oxygen balance fuel of the present invention desirably provides the capability of self-deflagration similar to a solid monopropellant. In addition, the high oxygen balance fuel of the present invention permits the use of much lower concentrations of oxidizer components and results in a much lower concentration of solid combustion products and greater gas output, which is particularly advantageous for volume limited systems. As a result, the high oxygen balance fuel of the present invention has applications in both of the systems set forth above and illustrated generally in FIGS. 1 and 2.

Although the yellow colored solid reaction product of aminoguanidine nitrate and nitric acid is assumed to be azodiformamidine dinitrate (azobisformamidine dinitrate), this invention is not limited only to this specific high oxygen balance fuel. The invention is also directed specifically to azodiformamidine dinitrate (azobisformamidine dinitrate). However, for simplicity, use of the term AZODN below refers both to the reaction product and azodiformamidine dinitrate in anhydrous and hydrous versions, unless specifically indicated otherwise.

A comparison of the high oxygen balance fuel of the present invention, namely, AZODN, with other high oxygen balance fuels shows that AZODN has a higher oxygen balance to carbon dioxide and water than other high oxygen balance fuels, as provided in Table 1.

TABLE 1

| Oxygen balance to $CO_2$ and $H_2O$ for HOB Fuels | |
|---|---|
| Compound | Oxygen Balance to $CO_2$ and $H_2O$ |
| Azobisformamidine dinitrate (AZODN), $C_2H_8N_8O_6$ | −13.3% |
| Ethylenediamine dinitrate (EDDN), $C_2H_{10}N_4O_6$ | −25.8% |
| Guanidine nitrate (GN), $CH_6N_4O_3$ | −26.2% |

The better oxygen balance of AZODN of the present invention over that of other high oxygen balance fuels, such as guanidine nitrate, permits the use of a lower concentration of oxidizer to maintain a desired 0.90/1 to 1.1/1 oxygen to fuel (O/F) balance in a resulting gas generant composition. However, if a gas generant is desired that is totally or essentially free of solid combustion product, an oxidizer, such as either phase stabilized or non-phase stabilized ammonium nitrate, can be utilized with the high oxygen balance fuel of the present invention. In such a case, the fuel of the present invention should be present as 40–60 wt % of the total gas generant composition. The use of AZODN of the present invention in either the form of the reaction product of aminoguanidine nitrate and nitric acid or, specifically, azobisformamidine dinitrate, produces higher gas outputs and less solid combustion products.

As provided in Table 2 below, the prior art fuels, such as 5-aminotetrazole (5ATZ)(discussed above in the Background of the Invention), guanidine nitrate (GN), and ethylenediaminedinitrate (EDDN), require a greater amount of strontium nitrate (SrN) in order to reach a 0.95/1 oxygen to fuel (O/F) balance. Moreover, gas generant compositions including these fuels produce less gas output and more solid combustion products than gas generant compositions including AZODN of the present invention.

TABLE 2

Comparison of High Oxygen Balance (HOB) Fuels With SrN*

| Fuel | SrN/Fuel | Flame Temp. (K.) | Gas Output | Solid Combustion |
|---|---|---|---|---|
| AZODN | 21.8/78.2 | 2734 | 32.4 | 12.5 |
| EDDN | 36.5/63.5 | 2546 | 32.4 | 17.9 |
| GN | 37.5/62.5 | 2236 | 30.6 | 21.6 |
| 5ATZ | 37.9/62.1 | 2700 | 24.8 | 31.2 |

O/F = 0.95/1

As demonstrated by the results set forth in Table 2, the compositions including EDDN, GN and 5ATZ required greater than 10% by weight more SrN than the composition including the high oxygen balance fuel (AZODN) of the present invention to provide the given 0.95/1 O/F ratio. Although 5ATZ exhibited a similar flame temperature as the present invention, the gas output was significantly lower and the content of solid combustion products was more than twice as high for the composition including 5ATZ as compared with the composition including AZODN.

If tailoring of the ballistics is anticipated, partial substitution of potassium perchlorate (KP) for strontium nitrate can be done. Under these conditions, the formation of solid combustion products decreases even further, as provided in Table 3.

TABLE 3

Partial substitution of KP for SrN with HOB Fuels

| Fuel | SrN/KP/Fuel | Flame Temp. (K.) | Gas Output | Solid Combustion |
|---|---|---|---|---|
| AZODN | 10.0/10.2/79.8 | 2792 | 32.9 | 11.2 |
| EDDN | 17.1/17.1/65.8 | 2615 | 32.6 | 17.6 |
| GN | 17.6/17.6/64.8 | 2304 | 32.7 | 18.1 |

Still, however, compositions including EDDN and GN as fuel, required significantly more potassium perchlorate and strontium nitrate than in the composition including AZODN. Although the gas output for all three of the above compositions were similar to one another, the solid combustion products production for the composition utilizing AZODN was much lower. Consequently, the gas generant of the present invention including AZODN is preferred for pyrotechnic gas generator systems as illustrated in FIGS. 1 and 2.

Compositions including the high oxygen balance fuel of the present invention (AZODN) and oxidizers are provided below in Tables 4–7 for accomplishing the desired O/F balance of 0.90/1 to 1.1/1. Specifically, compositions including AZODN and ammonium nitrate (AN) are provided in Table 4; AZODN, ammonium perchlorate (AP) and strontium nitrate (SrN) are provided in Table 5; AZODN, ammonium perchlorate (AP) and sodium nitrate (SN) are provided in Table 6; and AZODN, ammonium perchlorate (AP) and potassium nitrate (KN) are provided in Table 7. It should be noted that, although the compositions of Table 4 are hygroscopic, the production of solid combustion products is still very nil. In addition, the use of phase stabilized ammonium in nitrate is preferred.

TABLE 4

AZODN and Ammonium Nitrate Compositions

| AZODN (wt %) | AN (wt %) | O/F Balance |
|---|---|---|
| 75 | 25 | .9/1 |
| 67.35 | 32.65 | .95/1 |
| 60 | 40 | 1.0/1 |
| 52.94 | 47.06 | 1.05/1 |
| 46.15 | 53.85 | 1.1/1 |

TABLE 5

AZODN, Ammonium Perchlorate, and Strontium Nitrate Compositions

| AZODN (wt %) | AP (wt %) | SrN | O/F Balance |
|---|---|---|---|
| 82.3 | 9.3 | 8.4 | .9/1 |
| 77.4 | 11.9 | 10.7 | .95/1 |
| 72.9 | 14.3 | 12.8 | 1.0/1 |
| 69.2 | 16.5 | 14.3 | 1.05/1 |
| 64.8 | 18.5 | 16.7 | 1.1/1 |

TABLE 6

AZODN, Ammonium Perchlorate, and Sodium Nitrate Compositions

| AZODN (wt %) | AP (wt %) | SN | O/F Balance |
|---|---|---|---|
| 83.7 | 9.5 | 6.8 | .9/1 |
| 79.1 | 12.1 | 8.8 | .95/1 |
| 74.8 | 14.6 | 10.6 | 1.0/1 |
| 70.8 | 16.9 | 12.3 | 1.05/1 |
| 67.0 | 19.1 | 13.9 | 1.1/1 |

TABLE 7

AZODN, Ammonium Perchlorate, and Potassium Nitrate Compositions

| AZODN (wt %) | AP (wt %) | KN | O/F Balance |
|---|---|---|---|
| 82.6 | 9.3 | 8.1 | .9/1 |
| 77.8 | 11.9 | 10.3 | .95/1 |
| 77.3 | 14.3 | 12.4 | 1.0/1 |
| 69.2 | 16.5 | 14.3 | 1.05/1 |
| 65.3 | 18.6 | 16.1 | 1.1/1 |

In order to better understand the function of the high balance fuel of the present invention, examples of theoretical reactions of AZODN of the present invention are provided below wherein the structural formula for the AZODN is as follows:

and the molecular formula is:

$C_2H_8N_8O_6$ (1) Neat AZODN as a monopropellant for use in hybrid or ignition systems:

| | | | | |
|---|---|---|---|---|
| $C_2H_8N_8O_6 \rightarrow$ | $4H_2O\ +$ | $2CO\ +$ | $4N_2$ | |
| 240 | 72 | 56 | 112 = 240 | |
| 100.0% | 30.0% | 23.33% | 46.67% | |
| | 1.667M | 0.833M | 1.667M | |

Total Gas Output: 100.0 Wt. %
Total Gas Output (Moles): 4.167 Moles/100 Gms.
Total Solid Combustion Products: Zero Wt. %

(2) AZODN with ammonium nitrate (normal or phase stabilized):

| | | | | | |
|---|---|---|---|---|---|
| $2C_2H_8N_8O_6\ +$ | $3NH_4NO_3 \rightarrow$ | $14H_2O\ +$ | $3CO_2\ +$ | $CO\ +$ | $11N_2$ |
| 480 | 240 | 252 | 132 | 28 | 308 = 720 |
| 66.67% | 33.33% | 35.00% | 18.33% | 3.89% | 42.78% |
| | | 1.944M | 0.417M | 0.139M | 1.528M |

Total Gas Output: 100.0 Wt. % (O/F = 1.00) 100.0 Wt. % (O/F = 0.95)
Total Gas Output (Moles): 4.04 Moles/100 Gms.
Total Solid Combustion Products: Zero Wt. %

(3) AZODN with lithium nitrate and ammonium perchlorate:

| | | | | | | |
|---|---|---|---|---|---|---|
| $5C_2H_8N_8O_6\ +$ | $2LiNO_3\ +$ | $2NH_4ClO_4 \rightarrow$ | $2LiCl\ +$ | $24H_2O\ +$ | $10CO_2\ +$ | $22N_2$ |
| 1200 | 138 | 234 | 84 | 432 | 440 | 616 = 1572 |
| 76.33% | 8.78% | 14.89% | 5.34% | 27.48% | 27.99% | 39.19% |
| | | | 0.127M | 1.53M | 0.636M | 1.400M |

Total Gas Output: 94.7 Wt % (O/F = 1.00) 95.6 Wt % (O/F = 0.95)
Total Gas Output (Moles): 3.69 Moles/100 Gms.
Total Solid Combustion Products: 5.3 Wt. % (O/F = 1.00) 4.4 Wt % (O/F = 0.95)

(4) AZODN with sodium nitrate and ammonium perchlorate:

| | | | | | | |
|---|---|---|---|---|---|---|
| $5C_2H_8N_8O_6\ +$ | $2NaNO_3\ +$ | $2NH_4ClO_4 \rightarrow$ | $2NaCl\ +$ | $24H_2O\ +$ | $10CO_2\ +$ | $22N_2$ |
| 1200 | 170 | 234 | 116 | 432 | 440 | 616 = 1604 |
| 74.81% | 10.60% | 14.59% | 7.23% | 26.93% | 27.43% | 38.41% |
| | | | 0.125M | 1.50M | 0.623M | 1.372M |

Total Gas Output: 92.8 Wt % (O/F = 1.00) 93.8 Wt % (O/F = 0.95)
Total Gas Output (Moles): 3.50 Moles/100 Gms
Total Solid Combustion Products: 7.2 Wt % (O/F = 1.00) 6.2 Wt % (O/F = 0.95)

(5) AZODN with potassium nitrate and ammonium perchlorate

| | | | | | | |
|---|---|---|---|---|---|---|
| $5C_2H_8N_8O_6\ +$ | $2KNO_3\ +$ | $2NH_4ClO_4 \rightarrow$ | $2KCl\ +$ | $24H_2O\ +$ | $10CO_2\ +$ | $22N_2$ |
| 1200 | 202 | 234 | 148 | 432 | 440 | 616 = 1636 |
| 73.35% | 12.35% | 14.30% | 9.05% | 26.41% | 26.89% | 37.65% |
| | | | 0.122M | 1.467M | 0.611M | 1.345M |

Total Gas Output: 91.0 Wt % (O/F = 1.00) 92.0 Wt % (O/F = 0.95)
Total Gas Output (Moles): 3.42 Moles/100 Gms
Total Solid Combustion Products: 9.0 Wt % (O/F = 1.00) 8.0 Wt % (O/F = 0.95)

(6) AZODN with strontium nitrate and ammonium perchlorate:

| | | | | | | |
|---|---|---|---|---|---|---|
| $5C_2H_8N_8O_6\ +$ | $Sr(NO_3)_2\ +$ | $2NH_4ClO_4 \rightarrow$ | $SrCl_2\ +$ | $24H_2O\ +$ | $10CO_2\ +$ | $22N_2$ |
| 1200 | 212 | 234 | 157 | 432 | 440 | 616 = 1645 |
| 72.90% | 12.89% | 14.21% | 9.54% | 26.26% | 26.75% | 37.45% |
| | | | 0.061M | 1.459M | 0.608M | 1.338M |

Total Gas Output: 90.5 Wt % (O/F = 1.00) 92.0 Wt % (O/F = 0.95)
Total Gas Output (Moles): 3.405 Moles/100 Gms.
Total Solid Combustion Products: 9.5 Wt % (O/F = 1.00) 8.0 Wt % (O/F = 0.95)

(7) AZODN with lithium carbonate coolant and ammonium perchlorate:

| | | | | | | | | | |
|---|---|---|---|---|---|---|---|---|---|
| $14C_2H_8N_8O_6\ +$ | $9NH_4ClO_4\ +$ | $5Li_2CO_3 \rightarrow$ | $9LiCl\ +$ | $1/2Li_2O\ +$ | $74H_2O\ +$ | $27CO_2\ +$ | $6CO\ +$ | $60½N_2\ +$ | $¼O_2$ |
| 3360 | 1053 | 370 | 378 | 15 | 1332 | 1188 | 168 | 1694 | 8 = 4783 |
| 70.25% | 22.01% | 7.74% | 7.90% | 0.31% | 27.85% | 24.84% | 3.51% | 35.42% | 0.17% |
| | | | .188M | .010M | 1.547M | .565M | .125M | 1.265M | .005M. |

Total Gas Output: 91.79 Wt % (O/F = 1.00) 92.00 Wt % (O/F = 0.95)
Total Gas Output (Moles): 3.51 Moles/100 Gms. 3.73 Moles/100 Gms
Total Solid Combustion Products: 8.20 Wt. % (O/F = 1.00) 8.00 Wt. % (O/F = 0.95)

(8) AZODN with scandium nitrate and ammonium perchlorate:

| | | | | | | | |
|---|---|---|---|---|---|---|---|
| $2C_2H_8N_8O_6\ +$ | $⅓Sc(NO_3)_3\ +$ | $⅔NH_4ClO_4 \rightarrow$ | $⅓ScC_{12}\ +$ | $9⅓H_2O\ +$ | $4CO_2\ +$ | $9N_2\ +$ | $⅙O_2$ |
| 480 | 77 | 78 | 38 | 167.4 | 176 | 251 | 2.6 = 635 |
| 75.59% | 12.13% | 12.28% | 5.98% | 26.36% | 27.72% | 39.53% | 0.41% |
| | | | 0.05M. | 1.46M. | 0.63M. | 1.41M. | 0.01M |

-continued

| | | | | | |
|---|---|---|---|---|---|
| Total Gas Output: | | 94.0 Wt. % (O/F = 1.00) | | 3.51 Moles/100 Gms (O/F = 1.00) | |
| Total Solid Combustion Products: | | 6.0 Wt. % (O/F = 1.00) | | | |
| (9) AZODN with sodium nitrate: | | | | | |
| $5C_2H_8N_8O_6$ + | $4NaNO_3 \rightarrow$ | $2Na_2O$ + | $20H_2O$ + | $10CO_2$ + | $22N_2$ |
| 1200 | 340 | 124 | 360 | 440 | 616 = 1540 |
| 77.92% | 22.08% | 8.05% | 23.38% | 28.57% | 40.00% |
| | | 0.130M | 1.299M | 0.649M | 1.429M |
| Total Gas Output: | | 92.0 Wt. % (O/F = 1.00) | | 93.0 Wt. % (O/F = 0.95) | |
| Total Gas Output (Moles): | | | 3.38 Moles/100 Gms. | | |
| Total Solid Combustion Products: | | 8.0 Wt. % (O/F = 1.00) | | 7.00 Wt. % (O/F = 0.95) | |
| (10) AZODN with strontium nitrate: | | | | | |
| $5C_2H_8N_8O_6$ + | $2Sr(NO_3)_2 \rightarrow$ | $2SrO$ + | $20H_2O$ + | $10CO_2$ + | $22N_2$ |
| 1200 | 424 | 208 | 360 | 440 | 616 = 1624 |
| 73.89% | 26.11% | 12.81% | 22.17% | 27.09% | 37.93% |
| | | 0.123M | 1.232M | 0.616M | 1.355M |
| Total Gas Output: | | 87.2 Wt. % (O/F = 1.00) | | 89.3 Wt. % (O/F = 0.95) | |
| Total Gas Output (Moles): | | | 3.20 Moles/100 Gms. | | |
| Total Solid Combustion Products: | | 12.8 Wt. % (O/F = 1.00) | | 10.7 Wt. % (O/F = 0.95) | |
| (11) AZODN with potassium perchlorate: | | | | | |
| $2C_2H_8N_8O_6$ + | $KClO_4 \rightarrow$ | $KCl$ + | $8H_2O$ + | $4CO_2$ + | $8N_2$ |
| 480 | 138 | 74 | 144 | 176 | 224 = 618 |
| 77.67% | 22.33% | 11.97% | 23.30% | 28.48% | 36.25% |
| | | 0.162M | 1.294M | 0.647M | 1.295M |
| Total Gas Output: | | 88.03 Wt. % (O/F = 1.00) | | 89.90 Wt. % (O/F = 0.95) | |
| Total Gas Output (Moles): | | 3.24 Moles/100 Gms. | | 3.56 Moles/100 Gms | |
| Total Solid Combustion Products: | | 11.97 Wt. % (O/F = 1.00) | | 10.10 Wt. % (O/F = 0.95) | |
| (12) AZODN with aminoguanidine hexanitratocerate: | | | | | |
| $CeC_2H_{12}N_{14}O_{18}$ + | $3C_2H_8N_8O_6 \rightarrow$ | $CeO_2$ + | $18H_2O$ + | $8CO_2$ + | $19N_2$ |
| 660 | 720 | 172 | 324 | 352 | 532 = 1380 |
| 47.82% | 52.18% | 12.46% | 23.48% | 25.51% | 38.55% = 100% |
| Total Gas Output: | | | 87.54% | | |
| Total Solid Combustion Products: | | | 12.46% | | |
| (13) AZODN with aminoguanidine hexanitratocerate: | | | | | |
| $ScC_2H_{12}N_{14}O_{18}$ + | $3C_2H_8N_8O_6 \rightarrow$ | $ScO_2$ + | $18H_2O$ + | $8CO_2$ + | $19N_2$ |
| 565 | 720 | 77 | 324 | 352 | 532 = 1285 |
| 43.97% | 56.03% | 5.99% | 25.21% | 27.39% | 41.40% = 100% |
| Total Gas Output: | | | 94.01% | | |
| Total Solid Combustion Products: | | | 5.99% | | |

As provided by the above theoretical reactions of AZODN, a substantial gas output is possible by utilizing the fuel of the present invention. In most cases, the gas output is over 90 wt %. Even at the greater level of solid combustion products formed, the gas generant of the present invention utilizing AZODN produces less solid combustion products than prior gas generant compositions.

The specific process of obtaining the resulting reaction product of the present invention from the reaction of aminoguanidine nitrate and nitric acid is provided below. Further, use of this resulting reaction product with various additives are also provided to demonstrate the advantageous features thereof. Consequently, the term AZODN as used in the examples provided below refers to the actual yellow precipitate of Example 1.

EXAMPLE 1

The high oxygen balance fuel of the present invention was prepared by the following method. First, 10 grams of aminoguanidine nitrate (AGN) was weighed into a 400 ml glass beaker. Then, water, preferably distilled, up to about 20–25 ml volume was added whereupon a slurry of AGN/water resulted. A dispersion was formed by slowly pouring 150 ml of reagent grade nitric acid (70%), while stirring, into the AGN/water slurry, which brought the total volume up to about 170–175 ml. A 10 degree temperature rise occurred as the acid was first added. As the acid was continually added, the temperature came back down. The dispersion was then heated to 55–65° C. with moderate stirring on a hot plate. This caused any remaining AGN to go into solution.

Heating was continued at 55–65° C. during which time the solution went through a color transition from a water-white color to a straw color to an intensely bright yellow color (resembling the color of a solution of potassium dichromate). [Use of a hood and a ready ice bath are strongly suggested.] Moreover, the reaction should be limited to a temperature ceiling of below 65° C. It should be noted that the solution will turn a deeper yellow color just before exotherming.

The beaker was then placed in an ice bath to cool down the contents and allow the effervescence to subside. A yellow precipitate appeared as the temperature dropped below 12° C. after the reaction mixture was held in the ice bath at about 0–5° C. The yellow precipitate was vacuum filtered and washed with several rinses of distilled water. The precipitate was then washed several times with ethanol and then dried at 62° C.

EXAMPLE 2

Figure 3:
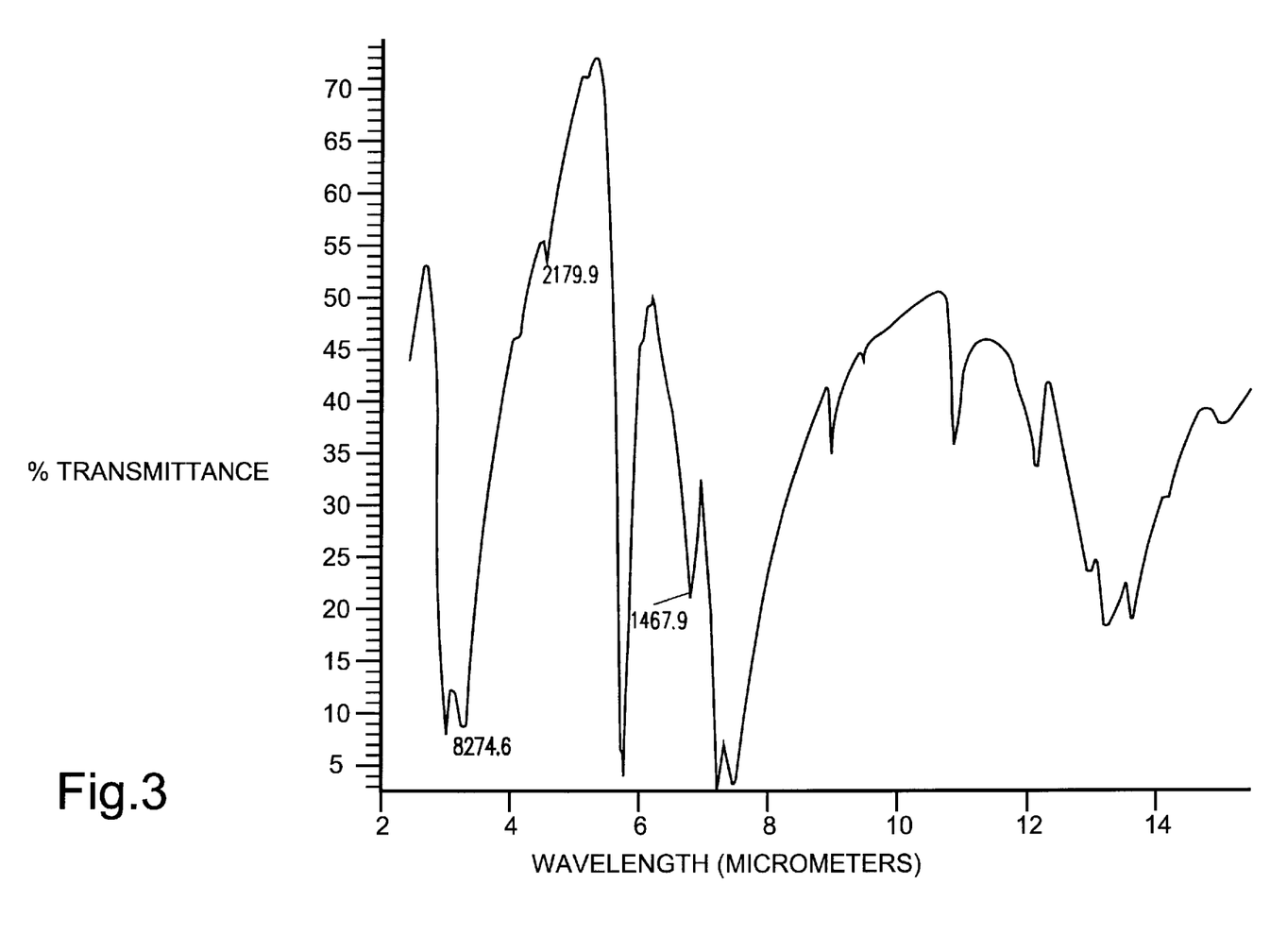
FIG. 3 is an infrared absorption spectra of the reaction product of the present invention.

The infrared absorption spectra for the reaction product formed from the procedure set forth in Example 1 was determined and is provided in FIG. 3. The absorption spectra was compared with the infrared absorption spectra from the literature taken from FIG. 2 of Anal. Chem.23, 1594 (1951).

A comparison of FIG. 3 with the reference spectra showed that the synthesized azobisformamidine-type reaction product of the present invention is considered to be 1,1'-azodiformamidine dinitrate (azodicarbamidine dinitrate).

EXAMPLE 3

Differential scanning calorimetry (DSC) was used to compare the thermal stability of the washed reaction product of Example 1 and a thermally aged reaction product (17 days at 107° C.). The DSC plots for the washed reaction product and the thermally aged reaction product showed that aging only slightly changed the material's exotherm peak and the material's exotherm onset. Specifically, the exotherm onset changed from 160.82° C. to 170.21° C. and the exotherm peak changed from 183.32° C. to 185.47° C. Consequently, the AZODN fuel of the present invention exhibits good aging characteristics.

EXAMPLE 4

Neat AZODN powder, produced by the method of Example 1, containing no oxidizers or other additives, self-deflagrated very rapidly when ignited at ambient temperature and pressure. Specifically, a small quantity (½ gram) of the high oxygen balance fuel of Example 1 was placed in a heap in the center of a watch glass and the flame of a burning splint was impinged on the sample. The sample immediately ignited and combusted very rapidly and cleanly similar to smokeless rifle powder. Such rapid self-deflagration makes the AZODN fuel of the present invention very beneficial for use in heterogeneous and/or hybrid inflators or auto-ignition pills (AIP's) and all-pyro gas generating systems.

EXAMPLE 5

A 0.269 gram quantity of AZODN of the present invention was placed in a pre-weighed aluminum pan and ignited with a burning splint. The pan was reweighed after igniting. Of the initial AZODN reaction product 0.005 grams of a tan residue remained, leaving a burn residual of 1.84% by weight.

Additional tests were performed on small propellant batches containing the AZODN reaction product of the present invention for determining sensitivity, thermal aging, weight loss, and ballistics properties. The density of the product and propellants made from the product was determined from the weight and pellet dimension measurements to be 1.66 g/cc or greater.

EXAMPLE 6

When ¼ inch×⅝ inch pressed pellets of neat AZODN of the present invention were burned in a strand bomb, without any oxidizer or other additives, they exhibited burning rates of 0.122, 0.342, and 0.428 inches per second (ips) at 100, 500, and 750 psi, respectively. These rates yielded a burning rate exponent of 0.63.

EXAMPLE 7

A propellant (Batch #11899) containing 10.60% sodium nitrate (SN) as an oxidizer and scavenger, 14.59% ammonium perchlorate (AP), and 74.81% AZODN of the present invention was formulated at an O/F ratio of 1.0 to provide, when combusted, 7% solid combustion products and 3.7 moles of substantially non-toxic gas per 100 grams of composition product. This formulation gave burning rates of 0.32 and 0.46 ips, respectively, at 500 and 750 psi. These rates yielded a pressure exponent of 0.90.

EXAMPLE 8

Another propellant (Batch #11900) containing 22.05% sodium nitrate (SN) oxidizer and 77.92% AZODN of the present invention was formulated to provide, when combusted, an 8% solid combustion products level and 3.4 moles of substantially non-toxic gas per 100 grams of composition. When ¼×⅝ inch pellets were tested for ballistic properties, burning rates at 250, 500, 750, 1000 and 1250 psi were respectively 0.17, 0.32, 0.47, 0.59, and 0.73 ips. These values yielded a pressure exponent of 0.90.

EXAMPLE 9

Another propellant (Batch #11901) containing 7.74% lithium carbonate (LC) scavenger and coolant, 22.01% AP oxidizer, and 70.25% AZODN of the present invention provided a burning rate of 0.34 ips at 500 psi but suffered severe weight loss of 5.9% after 24 hours at 107° C. The DSC for this formulation provided an onset temperature of 146° C. and an exotherm peak at 179° C.

EXAMPLE 10

A propellant (Batch #11903) containing weight percents of 12.35% potassium nitrate (KN) acting as a scavenger/oxidizer, 14.3% ammonium perchlorate (AP), and 73.35% AZODN of the present invention was formulated at an O/F ratio of 1.0 to provide on combustion, a theoretical solid combustion products level of 9% and 3.6 moles of substantially non-toxic gas per 100 grams of composition. When pressed into ¼×⅝ inch pellets and tested for ballistic properties, the formulation gave a burning rate of 0.40 and 0.52 ips at 500 and 750 psi, respectively, with a pressure exponent of 0.56.

EXAMPLE 11

Another propellant (Batch #11905) containing 12.89% strontium nitrate (SrN), 14.21% AP, and 72.90% AZODN of the present invention was formulated (with SrN acting as a clinker/scavenger/oxidizing agent) at an O/F ratio of 1.0 to provide, when combusted, a solid decomposition product level of 9.5% resulting in 3.5 moles of substantially non-toxic gas per 100 grams of composition. This mixture gave a burning rate of 0.34 and 0.61 ips at 500 and 1000 psi with a pressure exponent of 0.85.

Onset temperatures and exotherm peaks for the various propellant mixtures provided above are given in Table 8. These temperatures were obtained from DSC plots conducted for each of the above-noted batches.

TABLE 8

Exotherm Peak and Exotherm Onset Temperatures Observed via DSC

| Batch | Component | Composition (wt %) | Onset (° C.) | Peak (° C.) |
|---|---|---|---|---|
| Neat | AZODN | 100 | 161 | 183 |
| B11899 | AZODN | 74.8 | 158 | 182 |
|  | SN | 10.6 |  |  |
|  | AP | 14.6 |  |  |
| B11900 | AZODN | 77.9 | 158 | 181 |
|  | SN | 22.1 |  |  |
| B11901 | AZODN | 70.3 | 146 | 179 |
|  | LC | 7.7 |  |  |
|  | AP | 22.0 |  |  |
| B11903 | AZODN | 73.35 | 157 | 183 |
|  | KN | 12.35 |  |  |
|  | AP | 14.3 |  |  |

TABLE 8-continued

Exotherm Peak and Exotherm Onset Temperatures Observed via DSC

| Batch | Component | Composition (wt %) | Onset (° C.) | Peak (° C.) |
|---|---|---|---|---|
| B11905 | AZODN | 72.9 | 160 | 184.5 |
| | SrN | 12.9 | | |
| | AP | 14.2 | | |

The pressurized burn rates for the above Examples of AZODN propellants are provided below in Table 9.

TABLE 9

Pressurized Burn Rates for AZODN Propellants

| | Pressure | Burning Rate Inches per second at Pressure (Psia) | | | | | |
|---|---|---|---|---|---|---|---|
| Batch | Exponent | 100 | 250 | 500 | 750 | 1000 | 1250 |
| Neat AZODN | 0.63 | 0.12 | — | 0.34 | 0.43 | — | — |
| B11899 | 0.90 | — | — | 0.32 | 0.46 | — | — |
| B11900 | 0.90 | — | 0.17 | 0.32 | 0.47 | 0.59 | 0.73 |
| B11903 | 0.56 | — | — | 0.40 | 0.52 | — | — |
| B11905 | 0.85 | — | — | 0.34 | — | 0.61 | — |

Weight loss during aging is presented in Table 10 for the various AZODN formulations provided above.

TABLE 10

Pellet Weight Loss Vs. Days at Temperature

| | | Cumulative Weight Loss at Temperature | |
|---|---|---|---|
| Batch | Days at Temperature | 90° C. (%) | 107° C. (%) |
| Neat AZODN | 1 | 0.16 | 0.60 |
| | 3 | 0.41 | 1.09 |
| | 7 | 0.58 | 1.48 |
| | 13 | 0.64 | 1.65 |
| | 25 | 0.87 | 1.79 |
| B11899 | 1 | 0.27 | 0.54 |
| | 2 | 0.57 | 0.83 |
| | 3 | 0.62 | 0.98 |
| | 7 | 0.88 | 1.30 |
| | 16 | 1.08 | 1.66 |
| B11903 | 1 | 0.27 | 0.44 |
| | 2 | 0.39 | 0.62 |
| | 3 | 0.44 | 0.66 |
| | 7 | 0.61 | 0.96 |
| | 16 | 0.74 | 1.16 |
| B11905 | 1 | 0.23 | 0.43 |
| | 2 | 0.36 | 0.61 |
| | 3 | 0.42 | 0.78 |
| | 7 | 0.60 | 1.11 |
| | 16 | 0.78 | 1.43 |

Each of the above examples used filtered, washed and dried but unrecrystallized AZODN. Table 10 shows that very little weight is lost during accelerated aging at 107 and 90° C. The pellets (½ inch in diameter×½ inch in height) were dried at 62° C. (without a vacuum) prior to placing in either aging oven. Some weight loss occurs during the first day (24 hours) and is likely due to aqueous or non-aqueous volatile content.

EXAMPLE 12

Reformulation of the above propellant batches at an O/F ratio of 0.90 and 0.95 resulted in solid combustion products levels in the range of 6 to 7½%. Substitution of SN for a KN scavenger and oxidizer in AP/AZODN systems (where the scavenger inhibits formation of hydrogen chloride) resulted in solid combustion products levels of 6 and 4½% at O/F ratios of 0.95 and 0.90, respectively.

All of the propellant batches utilizing the high oxygen balance fuel of the present invention, as well as neat AZODN, responded with acceptable hazards properties with respect to impact, friction, and electrostatic sensitivity performed on powders. All propellant impact tests showed 10 negatives at 2.0 kg at 50 cm (100 kg-cm). All electrostatic discharge tests showed 10 negatives at six joules and 5 kV. All friction tests (type ABL) showed 10 negatives at 300 psi-90° with LC, SN and KN propellants (see examples below) showing 10 negatives at 1800 psi-90°.

Thermal stability studies, which included differential scanning calorimetry (DSC) and accelerated aging at elevated temperatures, were conducted on several batches containing the high oxygen balance product believed to be AZODN prepared according to Example 1. A DSC plot of a propellant respectively containing 12.9, 14.2, and 72.9 weight percentages of strontium nitrate (SrN), ammonium perchlorate (AP), and unrecrystallized AZODN showed an exothermic onset occurring at 161° C. with major decomposition at 184.5° C.

Differential scanning calorimetry (DSC) indicated the onset of exothermic decomposition to be about 160° C. for all of the above propellants. This suggests that an auto-ignition pill (AIP) may not be necessary with propellants containing the high oxygen balance fuel of the present invention or AZODN. Because neat AZODN and propellants containing AZODN possess low, but acceptable auto-ignition temperatures and acceptable pressure exponents combined with high burning rates at low operating pressures, this invention will be very effective for use volume limited, reduced weight inflator hardware. In addition, if manufactured from aluminum, high performance plastics, or lower gauge steel components, operation of an inflator using the propellants of the present invention will more likely pass bonfire tests that require an inflator to burst without fragmenting.

As can be seen from the above examples and corresponding testing, the high oxygen balance fuel of the present invention exhibits attractive propellant attributes and should be useful in a large number of pyrotechnic gas generant environments.

What is claimed is:

1. A pyrotechnic as generant composition comprising:
a high oxygen balance fuel in an amount of 67–84 wt. % which is a resulting solid yellow reaction product of aminoguanidine nitrate and nitric acid; and
an oxidizer system which includes 6–14 wt. % of sodium nitrate and 9–20 wt. % of ammonium perchlorate.

2. A pyrotechnic gas generant composition of claim 1, wherein said resulting yellow reaction product of aminoguanidine nitrate and nitric acid is prepared by a process comprising:
(a) providing aminoguanidine nitrate;
(b) combining said aminoguanidine nitrate with nitric acid to form a dispersion, wherein said dispersion proceeds through a color transition from water white to straw to bright yellow color, said color being comparable to a potassium dichromate solution.

3. A pyrotechnic gas generant composition of claim 2, wherein 70% reagent grade nitric acid is combined with said aminoguanidine nitrate.

4. A pyrotechnic gas generant composition of claim 1, wherein said resulting yellow reaction product of aminoguanidine nitrate and nitric acid is prepared by a process comprising:

(a) combining aminoguanidine nitrate and water to form a slurry;

(b) stirring 70% nitric acid into said slurry to form a dispersion;

(c) heating said dispersion during which time said dispersion dissolves and proceeds with effervescence through a color transition from water white to straw to a bright yellow color to form a solution, said bright yellow color being comparable to a potassium dichromate solution;

(d) cooling said solution to precipitate said solid yellow reaction product.

5. A pyrotechnic gas generant composition of claim 4, wherein said dispersion is heated to 55–65° C. and said solution is cooled to below 12° C.

6. A pyrotechnic gas generant composition of claim 1, wherein said oxidizer is substantially non-hygroscopic.

7. A pyrotechnic gas generant composition of claim 1, further including at least one additive selected from the group consisting of a scavenger, ignition aid, ignition initiator, gas conversion catalyst, ballistic modifier, slag formers, binders, energetic binders, plasticizers, energetic plasticizers, fuels, stabilizers, curing agents, cure catalysts, cross linkers, coolants, and compounding aids and mixtures thereof.

8. A pyrotechnic gas generant composition of claim 1, comprising 74.8 wt % of said high oxygen balance fuel, 10.6 wt % of said sodium nitrate and 14.6 wt % of said ammonium perchlorate, wherein said gas generant composition provides an exothern onset of 158° C. and an exotherm peak of 182° C.

9. A pyrotechnic gas generant composition comprising:

a high oxygen balance fuel in an amount of 73.35 wt. % which is a resulting solid yellow reaction product of aminoguanidine nitrate and nitric acid;

potassium nitrate in an amount of 12.35 wt. %; and ammonium perchlorate in an amount of 14.3 wt. %, wherein said gas generant composition provides an exotherm onset of 157° C. and an exotherm peak of 183° C.

10. A pyrotechnic gas generant composition comprising:

a high oxygen balance fuel in an amount of 72.9 wt. % which is a resulting solid yellow reaction product of aminoguanidine nitrate and nitric acid;

strontium nitrate in an amount of 12.9 wt. %; and ammonium perchlorate in an amount of 14.2 wt. %, wherein said gas generant composition provides an exotherm onset of 160° C. and an exotherm peak of 184.5° C.

11. A pyrotechnic gas generant composition comprising:

a high oxygen balance fuel in an amount of 65–83 wt. % which is a resulting solid yellow reaction product of aminoguanidine nitrate and nitric acid;

potassium nitrate in an amount of 8–17 wt. %; and ammonium perchlorate in an amount of 9–19 wt. %.

12. A pyrotechnic gas generant composition comprising:

a high oxygen balance fuel in an amount of 64–83 wt. % which is a resulting solid yellow reaction product of aminoguanidine nitrate and nitric acid;

strontium nitrate in an amount of 8–17 wt. %, and ammonium perchlorate in an amount of 9–19 wt. %.

13. A pyrotechnic gas generant composition comprising:

a high oxygen balance fuel in an amount of 70.3 wt. % which is a resulting solid yellow reaction product of aminoguanidine nitrate and nitric acid;

lithium carbonate in an amount of 7.7 wt. %; and ammonium perchlorate in an amount of 22.0 wt. %, wherein said gas generant composition provides an exotherm onset of 146° C. and an exotherm peak of 179° C.

14. A pyrotechnic as generant composition comprising:

a high oxygen balance fuel in an amount of 67–84 wt. % which is azodiformamidine dinitrate; and an oxidizer system which includes 6–14 wt. % of sodium nitrate and 9–20 wt. % of ammonium perchlorate.

15. A pyrotechnic gas generant composition of claim 14, wherein said oxidizer is substantially non-hygroscopic.

16. A pyrotechnic gas generant composition of claim 14, further including at least one additive selected from the group consisting of a scavenger, ignition aid, ignition initiator, gas conversion catalyst, ballistic modifier, slag formers, binders, energetic binders, plasticizers, energetic plasticizers, fuels, stabilizers, curing agents, cure catalysts, cross linkers, coolants, and compounding aids and mixtures thereof.

17. A pyrotechnic gas generant composition comprising:

a high oxygen balance fuel in an amount of 65–83 wt. % which is azodiformamidine dinitrate;

potassium nitrate in an amount of 8–17 wt. %, and ammonium perchlorate in an amount of 9–19 wt. %.

18. A pyrotechnic gas generant composition comprising:

a high oxygen balance fuel in an amount of 64–83 wt. % which is azodiformamidine dinitrate;

strontium nitrate in an amount of 8–17 wt. %; and ammonium perchlorate in an amount of 9–19 wt. %.

19. A pyrotechnic gas generant composition comprising:

azodiformamidine dinitrate (AZODN); and between 5 to 50 wt. % of an oxidizer system which comprises ammonium perchlorate and at least one additional oxidizer selected from the group consisting of sodium nitrate, potassium nitrate, strontium nitrate and lithium carbonate.

20. The pyrotechnic gas generant composition of claim 19, comprising 73.35 wt. % AZODN, 12.35 wt. % of said potassium nitrate, and 14.3 wt. % of said ammonium perchlorate.

21. The pyrotechnic gas generant composition of claim 19, comprising 72.9 wt. % AZODN, 12.9 wt. % of said strontium nitrate, and 14.2 wt. % of said ammonium perchlorate.

22. The pyrotechnic gas generant composition of claim 19, comprising 65–83 wt. % AZODN, 8–17 wt. % of said potassium nitrate, and 9–19 wt. % of said ammonium perchlorate.

23. The pyrotechnic gas generant composition of claim 19, comprising 64–83 wt. % AZODN, 8–17 wt. % of said strontium nitrate, and 9–19 wt. % of said ammonium perchlorate.

24. The pyrotechnic gas generant composition of claim 19, comprising 70.3 wt. % AZODN, 7.7 wt. % of said lithium carbonate, and 22.0 wt. % of said ammonium perchlorate.

* * * * *